(12) United States Patent
Hestad et al.

(10) Patent No.: US 9,186,185 B2
(45) Date of Patent: *Nov. 17, 2015

(54) BONE ANCHORING DEVICE

(71) Applicant: Zimmer Spine, Inc., Minneapolis, MN (US)

(72) Inventors: Hugh Hestad, Edina, MN (US); Kris Pauna, Prior Lake, MN (US)

(73) Assignee: Zimmer Spine, Inc., Edina, MN (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/083,555

(22) Filed: Nov. 19, 2013

(65) Prior Publication Data

US 2014/0066987 A1     Mar. 6, 2014

Related U.S. Application Data

(63) Continuation of application No. 13/205,110, filed on Aug. 8, 2011, now Pat. No. 8,636,770.

(51) Int. Cl.
*A61B 17/70*     (2006.01)
*A61B 17/80*     (2006.01)

(52) U.S. Cl.
CPC ........... *A61B 17/7053* (2013.01); *A61B 17/707* (2013.01); *A61B 17/7032* (2013.01); *A61B 17/7041* (2013.01); *A61B 17/7067* (2013.01); *A61B 17/8052* (2013.01); *A61B 17/8057* (2013.01); *A61B 17/8061* (2013.01)

(58) Field of Classification Search
CPC ........... A61B 17/7067; A61B 17/7053; A61B 17/7041
See application file for complete search history.

(56) References Cited

U.S. PATENT DOCUMENTS

| | | |
|---|---|---|
| 2,049,361 A | 7/1936 | Johan |
| 4,570,618 A | 2/1986 | Wu |
| 5,030,220 A | 7/1991 | Howland |
| 5,304,178 A | 4/1994 | Stahurski |
| 5,772,663 A | 6/1998 | Whiteside et al. |

(Continued)

FOREIGN PATENT DOCUMENTS

| | | |
|---|---|---|
| EP | 1205152 B1 | 9/2004 |
| WO | 0154599 A1 | 8/2001 |

(Continued)

OTHER PUBLICATIONS

U.S. Appl. No. 12/796,004, filed Jun. 8, 2010 (44 pages).

*Primary Examiner* — Ellen C Hammond
(74) *Attorney, Agent, or Firm* — Schwegman Lundberg & Woessner, P.A.

(57) ABSTRACT

A bone anchoring device including a clamping device and a flexible band configured to be secured a vertebra. The clamping device includes a base member and an upper member configured to be secured together with a fastener. The flexible band is configured to be passed around a bone portion and through a passage of the base member to position the flexible band between a clamping surface of the base member and a clamping surface of the upper member. The flexible band is tensioned to urge the clamping device against the bone portion and then clamped between the clamping surfaces of the base member and the upper member. A stabilization member of a vertebral stabilization construct may be secured to the vertebra with the bone anchoring device without invasively altering or impairing the structural integrity of the vertebra.

19 Claims, 17 Drawing Sheets

(56) References Cited

U.S. PATENT DOCUMENTS

| | | |
|---|---|---|
| RE36,221 E | 6/1999 | Breard |
| 5,935,133 A | 8/1999 | Wagner et al. |
| 5,964,769 A | 10/1999 | Wagner et al. |
| 6,053,921 A | 4/2000 | Wagner et al. |
| 6,086,590 A | 7/2000 | Margulies et al. |
| 6,179,838 B1 | 1/2001 | Fiz |
| 6,277,120 B1 | 8/2001 | Lawson |
| 6,299,613 B1 | 10/2001 | Ogilvie et al. |
| 6,309,390 B1 | 10/2001 | Le Couedic et al. |
| 6,391,030 B1 | 5/2002 | Wagner et al. |
| 6,514,255 B1 | 2/2003 | Ferree |
| 6,547,790 B2 | 4/2003 | Harkey, III et al. |
| 6,605,091 B1 | 8/2003 | Iwanski |
| 6,682,533 B1 | 1/2004 | Dinsdale et al. |
| 6,695,852 B2 | 2/2004 | Gleason |
| 7,481,828 B2 | 1/2009 | Mazda et al. |
| 7,959,654 B2 | 6/2011 | Mazda et al. |
| 8,128,635 B2 | 3/2012 | Belliard et al. |
| 2002/0116013 A1 | 8/2002 | Gleason et al. |
| 2003/0083746 A1* | 5/2003 | Kuslich .................. 623/17.11 |
| 2006/0241614 A1* | 10/2006 | Bruneau et al. ............ 606/69 |
| 2009/0105715 A1 | 4/2009 | Belliard et al. |
| 2009/0138048 A1 | 5/2009 | Baccelli et al. |
| 2009/0177233 A1 | 7/2009 | Malek |
| 2009/0182379 A1 | 7/2009 | Baccelli et al. |
| 2009/0248077 A1 | 10/2009 | Johns |
| 2009/0326585 A1 | 12/2009 | Baccelli et al. |
| 2010/0249845 A1 | 9/2010 | Meunier et al. |
| 2011/0034956 A1 | 2/2011 | Mazda et al. |
| 2011/0112581 A1 | 5/2011 | Clement |
| 2011/0238118 A1 | 9/2011 | Baccelli et al. |
| 2011/0238125 A1 | 9/2011 | Baccelli et al. |
| 2011/0301644 A1 | 12/2011 | Belliard |
| 2012/0022591 A1 | 1/2012 | Baccelli et al. |
| 2012/0022592 A1 | 1/2012 | Belliard |
| 2012/0059377 A1 | 3/2012 | Belliard |
| 2012/0130373 A1* | 5/2012 | Larroque-Lahitette ......... 606/74 |

FOREIGN PATENT DOCUMENTS

| | | |
|---|---|---|
| WO | 2002009604 A1 | 2/2002 |
| WO | 2011012690 A1 | 2/2011 |

\* cited by examiner

BONE ANCHORING DEVICE

CROSS-REFERENCES TO RELATED APPLICATIONS

The present application is a continuation application of U.S. patent application Ser. No. 13/205,110, filed Aug. 8, 2011, now U.S. Pat. No. 8,636,770, the entire contents of which is herein incorporated by reference.

TECHNICAL FIELD

The disclosure is directed to a device for anchoring to a bone. More particularly, the disclosure is directed to a clamping device for clamping to a bone without invasively altering or impairing the structural integrity of the bone.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column. In other instances, the spinal column may include an abnormal curvature, such as scoliosis, prompting remedial measures to attempt to correct or reduce the abnormal curvature.

One possible method of treating these conditions is to stabilize a portion of the spine to allow treatment, reduce curvature, and/or offload compressive loading along a portion of the spine. Traditionally, stabilization has been accomplished by securing a stabilization construct to two or more vertebrae using vertebral anchors, such as pedicle screws installed into bony portions of the vertebrae, such as the pedicles. In such instances, the vertebrae must be modified, such as by drilling holes into the bone, in order to install the pedicle screws, thus impairing the structural integrity of the vertebrae. In some instances, there may be insufficient bony anatomy in which to install a pedicle screw, thus preventing the use of conventional pedicle screw based stabilization constructs.

In some instances, however, it may be desirable or necessary to secure a stabilization construct to one or more vertebrae of a spinal segment, or another bony anatomy, without irreversibly altering or impairing the bone member to which the stabilization construct is secured to. Accordingly, it may be desirable to provide alternative bone anchoring devices which may be secured to one or more vertebrae of a spinal segment of a spinal column, or another bony anatomy, in a non-invasive manner without the use of a pedicle screw, or otherwise invasively altering or impairing the integrity of the bone member, thereby preserving the bony anatomy while still anchoring to the bone member.

SUMMARY

The disclosure is directed to several alternative designs, materials and methods of manufacturing medical device structures and assemblies, and uses thereof.

Accordingly, one illustrative embodiment is a bone anchoring device including a clamping device and a flexible band configured to be secured around a bone member. The clamping device includes a base member and an upper member configured to be secured together with a fastener. The base member has a clamping surface facing a clamping surface of the upper member. The flexible band has a first end and a second end. The flexible band is configured to be passed around a bone member to urge the clamping device against the bone member. The base member includes a passage for receiving the flexible band therethrough to position the flexible band between the clamping surface of the base member and the clamping surface of the upper member. The upper member includes a channel therethrough, offset from the passage in the base member, for receiving a stabilization member of a vertebral stabilization construct.

Another illustrative embodiment is a bone anchoring device for securing a stabilization member of a vertebral stabilization construct to a vertebra without invasively altering the vertebra. The bone anchoring device includes a clamping device and a flexible band. The clamping device includes a base member and an upper member configured to be secured together with a fastener. The base member has a bone engagement surface configured to engage a surface of the vertebra when secured thereto and a clamping surface. The upper member includes a clamping surface facing the clamping surface of the base member. The flexible band, which has a first end and a second end, is configured to be passed around a bony portion of the vertebra to secure the clamping device to the vertebra. The base member includes a passage for receiving the flexible band therethrough to position the flexible band between the clamping surface of the base member and the clamping surface of the upper member. The flexible band is configured to be clamped between the clamping surface of the base member and the clamping surface of the upper member independent of securing the stabilization member to the clamping device.

Yet another illustrative embodiment is a method of correcting the curvature of a spine. The method includes positioning a clamping device against a bone member of a first vertebra with a flexible band extending around the bone member. The clamping device includes a base member and an upper member securable to the base member with a fastener. The flexible band is clamped between a clamping surface of the base member and a clamping surface of the upper member with a first fastener to secure the clamping device to the first vertebra. A stabilization construct is then secured to the clamping device independent of clamping the flexible band between the base member and the upper member. The stabilization construct is also secured to a second vertebra to stabilize the first vertebra relative to the second vertebra.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
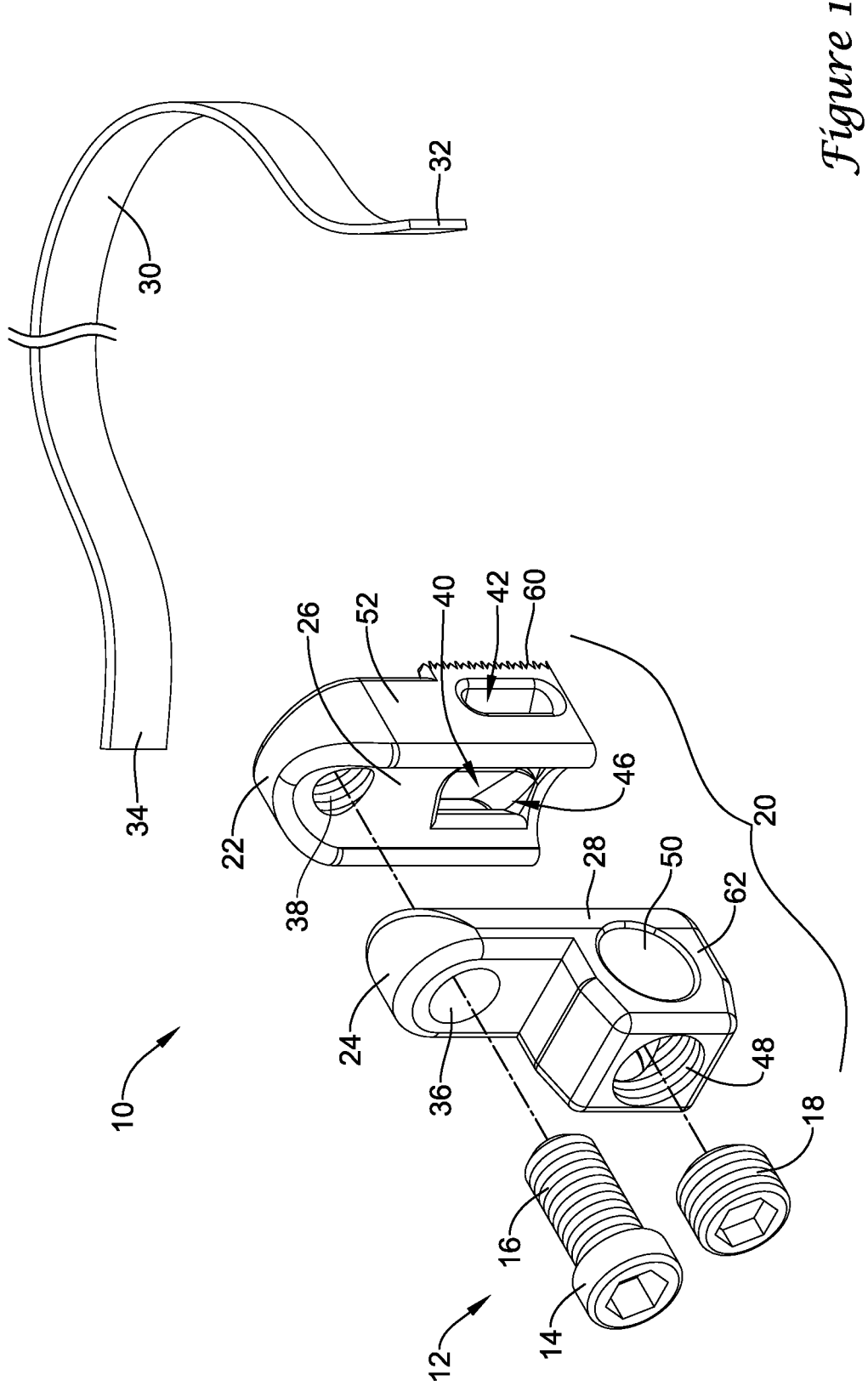
FIG. 1 is an exploded front perspective view of components of an exemplary bone anchoring device.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 2:
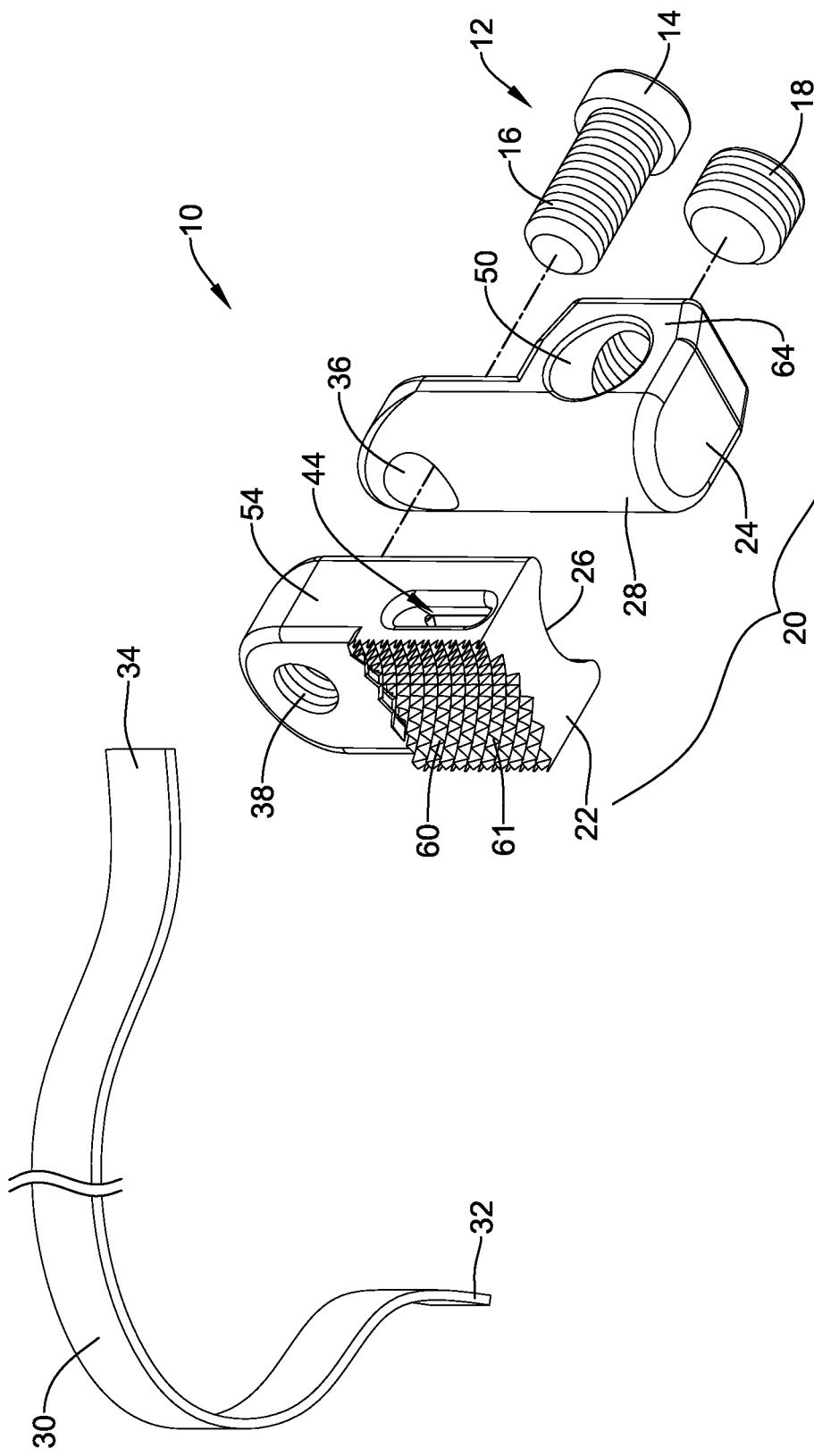
FIG. 2 is an exploded rear perspective view of components of the bone anchoring device of FIG. 1.

FIGS. 1 and 2 illustrate components of an exemplary bone anchoring device 10 configured to be secured to a bone member, such as a bony portion of a vertebra, without invasively damaging and/or altering the bone member, or otherwise compromising the structural integrity of the bone member. For instance, the bone anchoring device 10 may be secured to a bone member without drilling holes and/or installing a fastener, such as screwing a threaded fastener, into the bone member.

Although the bone anchoring device 10 is illustrated as being securable to a bone member of a vertebra, it is noted that the bone anchoring device 10 may be configured for use in a wide array of applications for musculoskeletal injuries, disorders, deformations, modifications, and treatments in which it is desirable to anchor to a bone member. Accordingly, the bone anchoring device 10 may be used for anchoring to any desired bony anatomy, such as a rib, clavicle, arm bone, leg bone, pelvis, etc.

The bone anchoring device 10 may include a clamping device 20 including a base member 22, an upper member 24 and a flexible strap or band 30 configured to be passed around a bony portion of a vertebra, or other bone member, to secure the clamping device 20 to the vertebra, or other bone member. The base member 22 and the upper member 24 may be configured to be secured together with a fastener 12, such as a threaded fastener, to clamp the flexible band 30 between a clamping surface 26 of the base member 22 and a clamping surface 28 of the upper member 24. In some instances, the clamping surface 26 of the base member 22 may be a concave surface and the clamping surface 28 of the upper member 24 may be a convex surface sized and configured to mate with the concave surface of the clamping surface 26 of the base member 22. For instance, radii of curvature of the clamping surfaces 26, 28 may be substantially equal in some instances. In other instances, the clamping surface 26 of the base member 22 may be a convex surface and the clamping surface 28 of the upper member 24 may be a concave surface sized and configured to mate with the convex surface of the clamping surface 28 of the base member 22, or the clamping surface 26 of the base member 22 may be otherwise sized and configured to mate with, or otherwise be complementary to, the clamping surface 28 of the upper member 24.

The base member 22 and the upper member 24 may be formed of any desired biocompatible material. For example, the base member 22 and/or the upper member 24 may be formed of a metallic material, such as titanium, stainless steel, or other biocompatible metal or metal alloy. Alternatively, the base member 22 and/or the upper member 24 may be formed of a polymeric material, such as polyetheretherketone (PEEK), or other biocompatible polymeric material. In some instances, the base member 22 and/or the upper member 24 may be formed of a combination or composite of metallic and polymeric materials.

The base member 22 may include a threaded bore 38 axially aligned with a bore 36 extending through the upper member 24 configured to receive the fastener 12 therethrough. The fastener 12 may include a head 14 and a threaded shank 16 extending therefrom configured to threadably engage interior threads of the threaded bore 38 of the base member 22. As the fastener 12 is threaded into the threaded bore 38, the head 14 may bear against the upper member 24 to exert a clamping force on the upper member 24 to clamp the upper member 24 to the base member 22. The mating contours of the clamping surfaces 26, 28 may maintain the upper member 24 aligned with the base member 22 as the fastener 12 clamps the members 22, 24 together. It is noted that other fasteners or clamping means are contemplated to clamp or otherwise secure the upper member 24 to the base member 22 and clamp the flexible band 30 therebetween.

The base member 22 may include an engagement surface 60 configured to engage or press against a surface of a bone when the clamping device 20 is secured to a bone. For instance, as discussed herein, the flexible band 30, extending around a bone member, may be drawn tight to force the engagement surface 60 against the bone member to secure the clamping member 20 to the bone member, such as a vertebra. The engagement surface 60 may have any desired curvature to match or generally follow the contour of the bony anatomy against which the engagement surface 60 is placed. For example, as shown in the figures, the engagement surface 60 may include a concave curvature configured to complement the curvature of a transverse process of a vertebra, a rib, or a long bone. In other instances, the curvature of the engagement surface 60 may include a convex curvature configured to complement the curvature of a pedicle or lamina, for example. Various contoured shapes for the engagement surface 60 are contemplated to complement the desired bony anatomy against which the engagement surface 60 is to be placed. In some instances, the engagement surface 60 may be a flat surface, if desired.

Figure 3:
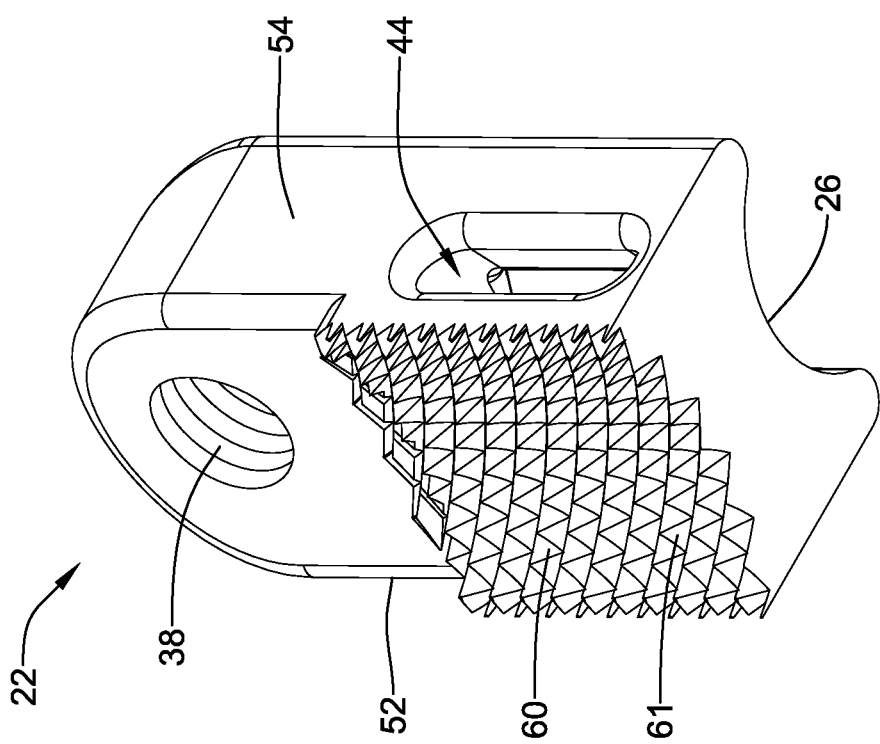
FIG. 3 is a lower perspective view of an exemplary base member of a clamping device.

In some instances, the engagement surface 60 may include engagement features 61 as shown in FIG. 3, such as spikes, teeth, ridges, protuberances, bumps, grooves, serrations, knurlings, surface rougheners, or other characteristics, configured to enhance the frictional engagement between the engagement surface 60 and the bony anatomy and/or prevent slippage therebetween. The engagement features 61 may be configured such as not to impair the integrity of the bony anatomy against which the engagement surface 60 is placed.

In some embodiments, the engagement surface 60 may include a layer of a porous metal defining a plurality of pores formed by a metallic scaffold. For instance, the porous metal material may be tantalum, titanium, zirconium, cobalt, chrome and stainless steel, or alloys thereof. In some instances, the pores of the porous metal will have a pore size of about 150 microns to about 500 microns, or more. However, in other instances a smaller pore size may be desired, such as a pore size of less than about 150 microns. The open cell structure of the porous layer of material may mimic the microstructure of a natural cancellous bone, acting as an osteoconductive matrix for the incorporation of bone, providing optimal permeability and high surface area to encourage new bone in-growth into the pores of the porous layer of material. Furthermore, the porous layer of material may have an elastic modulus similar to natural cancellous bone. For instance, depending on its porosity, the porous layer of material may have an elastic modulus of about 1.5 GPa to about 4 GPa, or about 3 GPa, whereas natural cancellous bone, depending on physiological factors of a specific patient, may have an elastic modulus of about 0.1 GPa to about 3 GPa, or about 0.5 GPa in many instances. The porous layer of material may provide a roughened surface with a high coefficient of friction against the bone member to resist migration of the clamping device 20 once clamped to the bone member.

One exemplary porous metal is Trabecular Metal™ material, which is a porous tantalum material marketed by Zimmer Spine, Inc. of Minneapolis, Minn. This material is also disclosed in several U.S. patents, including, for example, U.S. Pat. Nos. 5,282,861, 5,443,515, and 6,063,442, the disclosures of which are incorporated herein by reference. These patents describe the formation of a tantalum porous structure by chemical vapor deposition of tantalum onto a foam carbon structure.

The flexible band 30 may include a first end portion 32, a second end portion 34, and an intermediate portion between the first and second end portions 32, 34. In some instances, the flexible band 30 may have a flat or elongated cross-sectional shape, while in other embodiments the flexible band 30 may have a circular, oval, or other cross-sectional shape, as desired. The flexible band 30 may be formed of any desirable material and may have any desired construction. In some instances, the flexible band 30 may be configured to be substantially non-distensible, while in other embodiments the flexible band 30 may have sufficient elasticity to permit elongation of the flexible band 30 under tension. In some instances, the flexible band may be formed of interwoven fibers, such as Dacron® fibers, polyethylene-terephthalate (PET) fibers, or other polymeric material. However, it will be recognized that various other materials suitable for implantation within the human body and for providing securement to the bone member while maintaining flexibility may be used. In other embodiments, the flexible band 30 can be constructed of other flexible materials such as metal, polymeric materials, or combinations of flexible materials.

Figure 4:
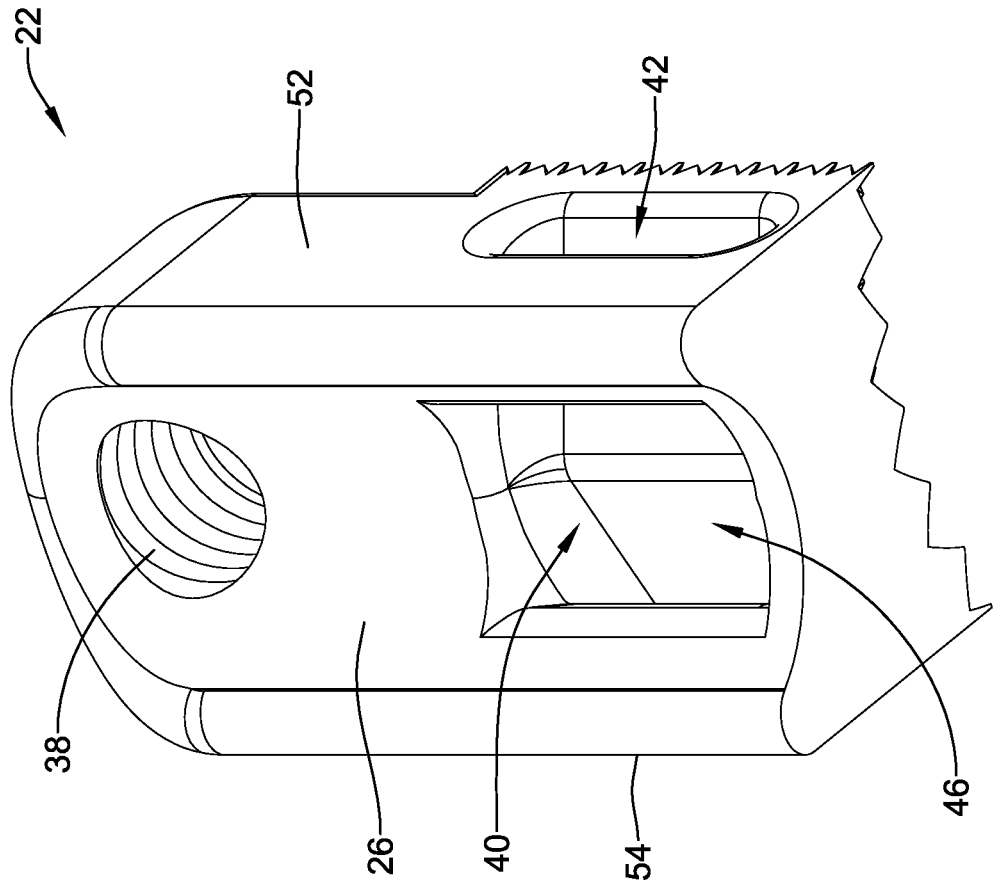
FIG. 4 is an upper perspective view of the base member of FIG. 3.
Figure 5:
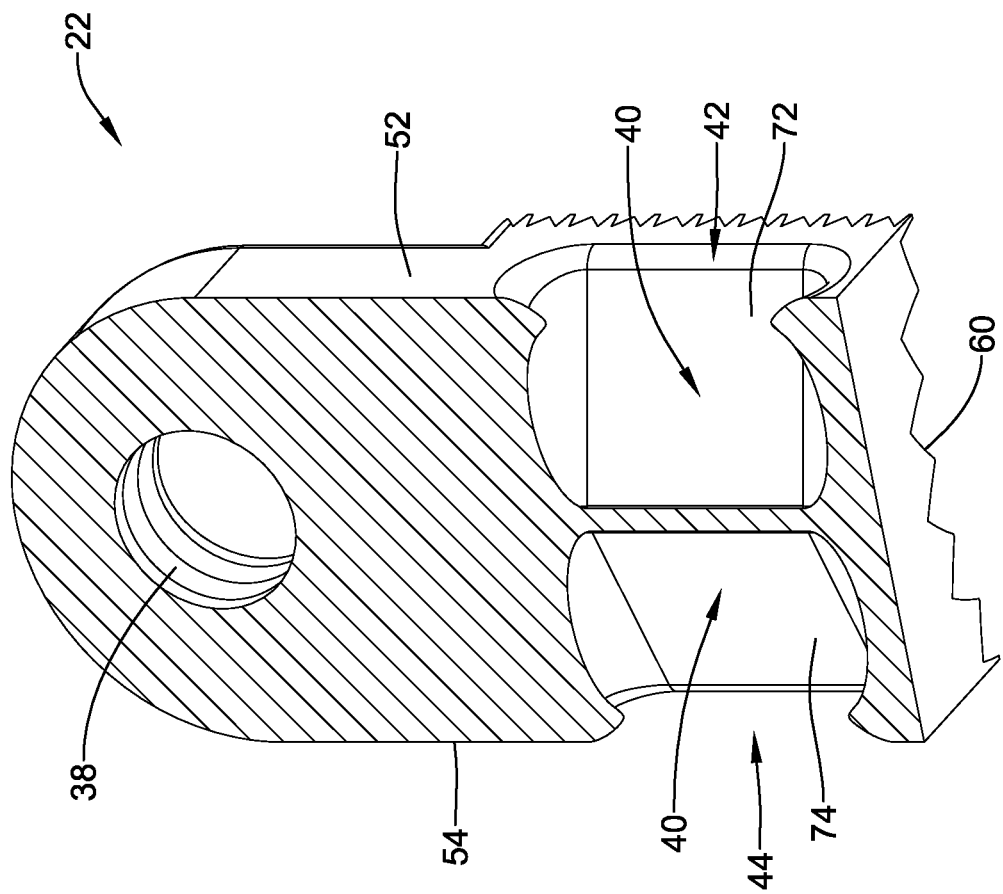
FIG. 5 is a cut-away view of the base member of FIG. 3.
Figure 6:
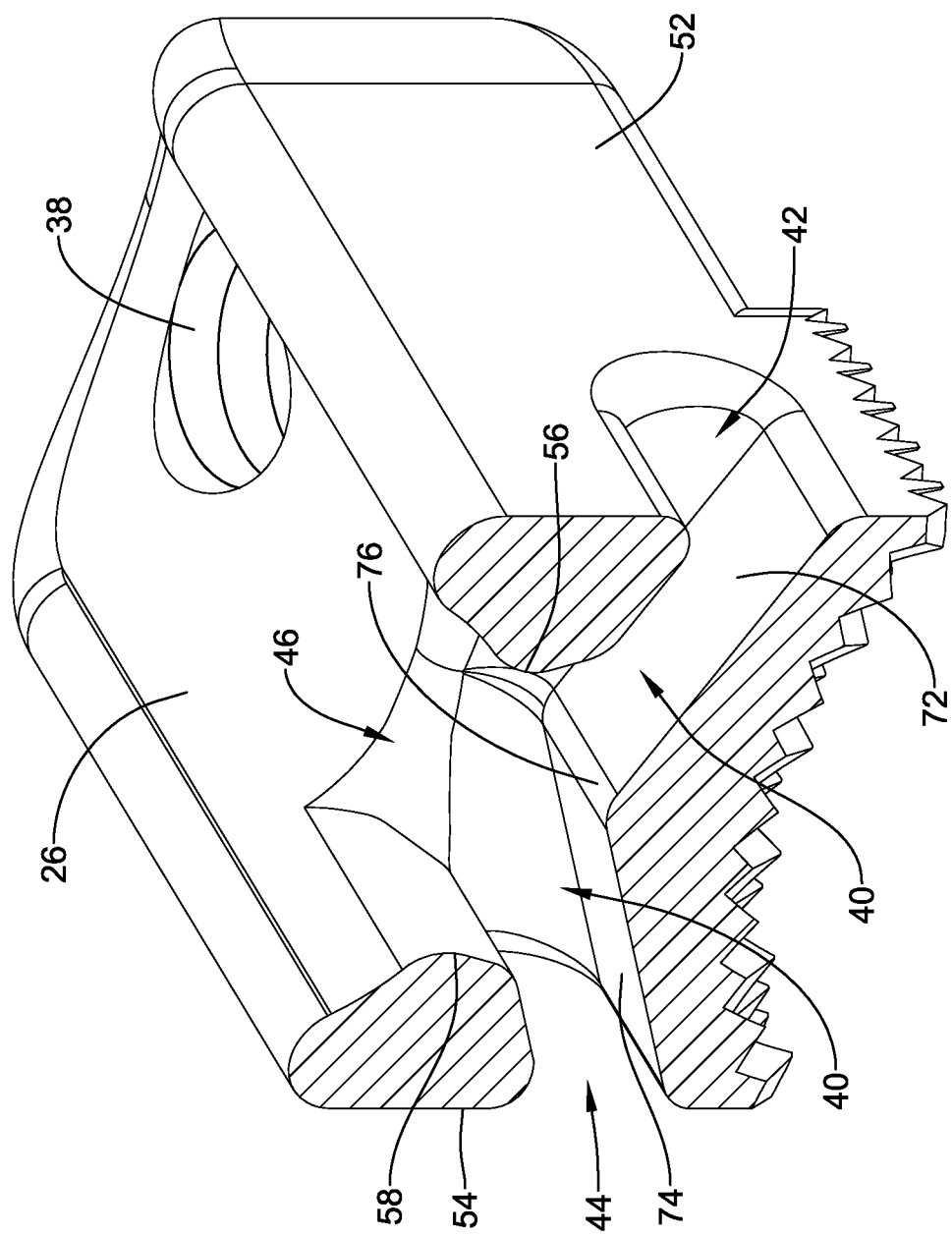
FIG. 6 is another cut-away view of the base member of FIG. 3.

The base member 22 may also include a passage 40, as shown in FIG. 4, extending through the base member 22 which is configured to receive a portion of the flexible band 30 therethrough. In some instances, the passage 40 of the base member 22 includes a first opening 42 on a first side 52 of the base member 22, a second opening 44 on a second side 54 of the base member 22, opposite the first side 52, and a third opening 46 on the concave clamping surface 26 extending between the first side 52 and the second side 54. Additional characteristics of the passage 40 are further illustrated in the cross-sectional view of FIGS. 5 and 6. For example, the passage 40 may include a first ramped surface 72 extending from the first opening 42 into the interior of the base member 22 and a second ramped surface 74 extending from the second opening 44 into the interior of the base member 22. The first ramped surface 72 may converge with the second ramped surface 74 toward the third opening 46 at a peak 76 proximate the third opening 46. Furthermore, the third opening 46 may be defined, at least in part, by a first edge or rim 56 and a second edge or rim 58 opposite the first rim 56. In some instances the rims 56, 58 may include convex surfaces converging with the concave clamping surface 26 of the base member 22.

Figure 7:
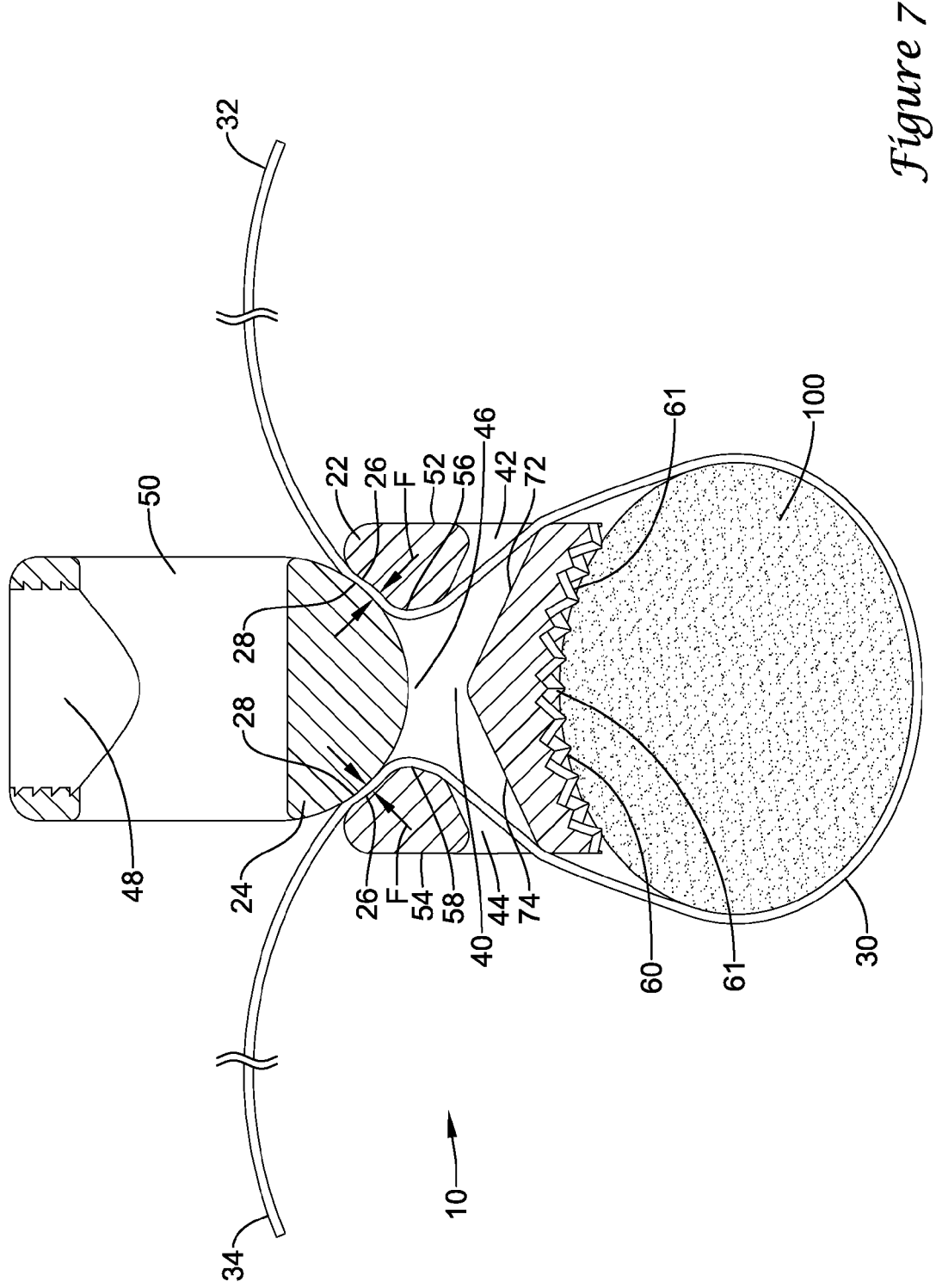
FIG. 7 is a cross-sectional view of the bone anchoring device secured to a bone member.

FIG. 7 is a cross-sectional view of the bone anchoring device 10 secured to a bone 100, illustrating the interaction of components of the bone anchoring device 10 to secure the bone anchoring device 10 to the bone 100. As shown in FIG. 7, a central portion of the flexible band 30 may extend around the bone 100 with the first and second end portions 32, 34 passing through the passage 40 of the base member 22. For example, the first end portion 32 of the flexible band 30 may enter the passage 40 through the first opening 42 and exit the passage 40 through the third opening 46. Similarly, the second end portion 34 of the flexible band 30 may enter the passage 40 through the second opening 44 and exit the passage 40 through the third opening 46. An intermediate portion of the flexible band 30 may form a loop between the first opening 42 and the second opening 44 configured to extend around the bone 100.

Providing the side openings 42, 44 on opposite sides of the base member 22 may permit the engagement surface 60 of the base member 22 to seat against the surface of the bone over a large surface area to provide enhanced engagement against the bone, while the flexible band 30 extends around the bone and into the base member 22. Thus, the flexible band 30 may not interfere with positioning the engagement surface 60 against the bone member.

The first end portion 32 of the flexible band 30 may pass from the third opening 46 and between the clamping surface 26 of the base member 22 and clamping surface 28 of the upper member 24 on a first side of the clamping device 20. Similarly, the second end portion 34 of the flexible band 30 may pass from the third opening 46 and between the clamping surface 26 of the base member 22 and clamping surface 28 of the upper member 24 on a second side of the clamping device 20, opposite the first side. The clamping surface 28 of the upper member 24 may extend across, and thus cover the third opening 46 of the passage 40.

A tensile force may be applied to the first and second end portions 32, 34 of the flexible band 30, such as with a tensioning tool, to draw the clamping device 20 against the bone 100 and cinch the intermediate portion of the flexible band 30 extending around the bone 100. As the engagement surface 60 of the base member 22 is pressed against the bone 100, the engagement features 61 may imbed into or otherwise grip the bone 100 to prevent slippage therebetween. When the flexible band 30 has been pulled sufficiently taut, the fastener 12 may be tightened into the threaded bore 38 of the base member 22, generating a clamping force F to thereby clamp the first and second end portions 32, 34 of the flexible band 30 between the clamping surface 26 of the base member 22 and the clamping surface 28 of the upper member 24. As can be seen in FIG. 7, with the flexible band 30 tightly pulled around the bone 100, the flexible band 30 presses against the rims 56, 58 of the third opening 46 as well as an edge of the first and second openings 42, 44 to further secure the flexible band 30 from loosening. Subsequently, excess portions of the first and second end portions 32, 34 of the flexible band 30 may be trimmed away if desired, or alternatively, portions of the first and second end portions 32, 34 may be extended to another device and/or bone portion, or otherwise used in a stabilization construct.

The upper member 24 of the clamping device 20 may be configured to be secured to a structural component of a stabilization construct extending from the bone anchoring device 10 secured to bone member (e.g., a vertebra) to one or more additional bone members (e.g., one or more additional vertebrae of the spinal column). For example, the upper member 24 may include a channel or other structure through which an elongate member of a stabilization construct may extend through to secure the elongate member to the clamping device 20. Accordingly, an elongate member of a stabilization construct may be secured to the clamping device 20 independent of clamping the flexible band 30 to the clamping device 20. In other words, the flexible band 30 may be clamped between the upper member 24 and the base member 22 without (e.g., prior to or subsequent to) securing the elongate member of a stabilization construct to the upper member 24, or vise versa, the elongate member of a stabilization construct may be secured to the upper member 24 without (e.g., prior to or subsequent to) clamping the flexible band 30 between the upper member 24 and the base member 22. In other words, two separate and independent actions are carried out to clamp the flexible band 30 and secure an elongate member of a stabilization construct, respectively, to the clamping device 20.

FIGS. 8-12 illustrate several variations of the upper member 24 to accommodate a variety of applications of the bone anchoring device 10. It is contemplated that during a medical procedure, medical personnel could select a desired configuration of the upper member 24 to be used with the clamping device 20 from an assortment of configurations supplied, based on the elongate member of the stabilization construct to be secured to the bone anchoring device 10. Although several variations of the upper member 24 are shown, additional variations configured to accommodate additional configurations of stabilization constructs are contemplated.

Figure 8:
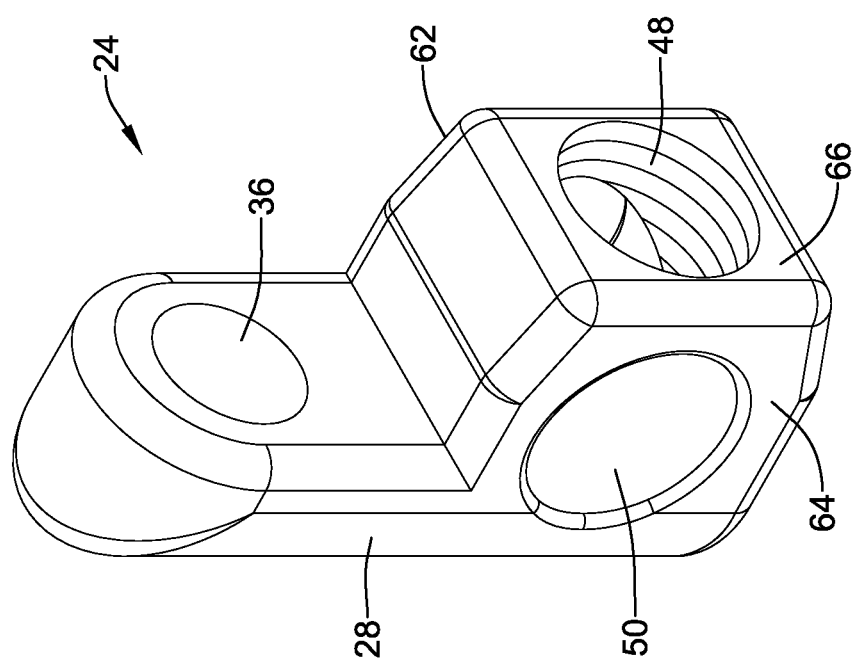
FIG. 8 is an upper perspective view of an exemplary upper member of a clamping device.
Figure 9:
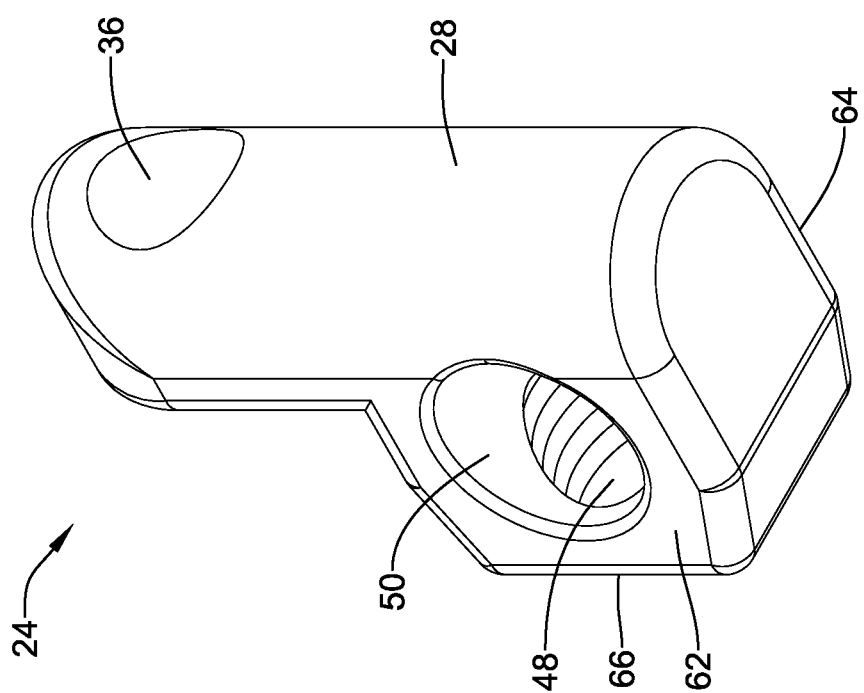
FIG. 9 is a lower perspective view of the upper member of FIG. 8.

A first configuration of an upper member 24 is illustrated in FIGS. 8 and 9. The upper member 24 includes a clamping surface 28, such as a convex surface, configured to mate with the clamping surface 26 of the base member 22 to clamp the flexible band 30 therebetween. The upper member 24 also includes a channel 50 extending through the upper member 24 from a first side 62 to a second side 64 configured to receive an elongate member, such as an elongate rod, of a stabilization construct therethrough. As shown in FIGS. 8 and 9, the channel 50 may be a through hole extending through the upper member 24 having a peripheral surface fully surrounding the channel 50. A threaded bore 48 having a longitudinal axis extending transverse (e.g., perpendicular) to a longitudinal axis of the channel 50 may intersect the channel 50. The threaded bore 48 may be configured to threadably engage the fastener 18 to bear against the elongate member extending through the channel 50 to secure the elongate member to the bone anchoring device 10 and lock the elongate member from axial and/or rotational movement relative to the upper member 24.

Figure 10:
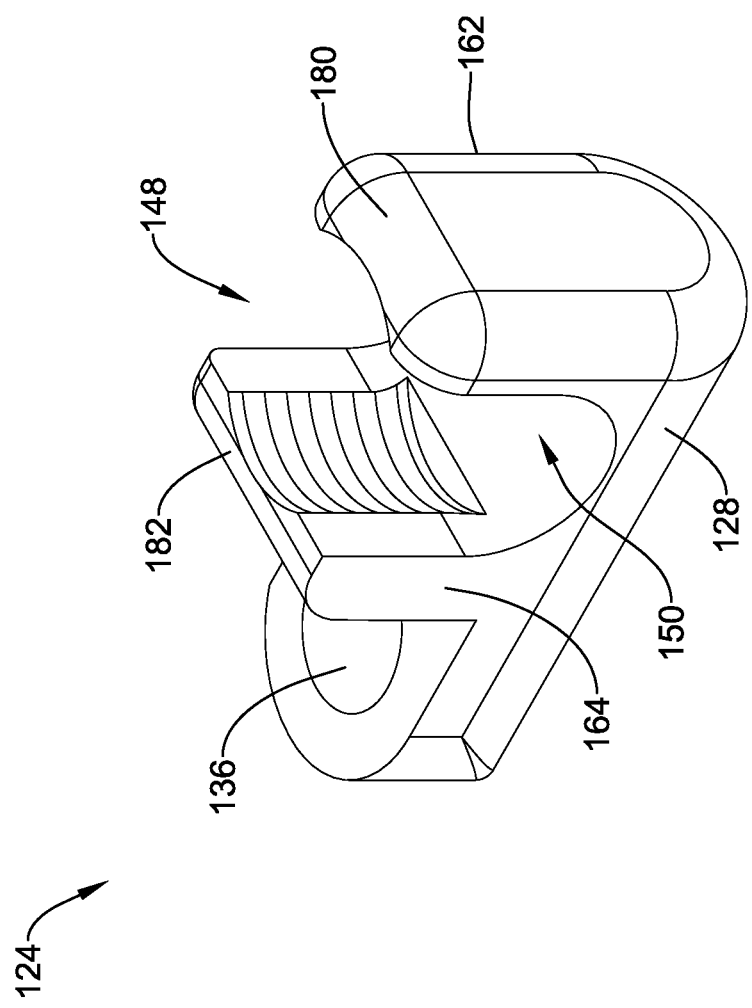
FIG. 10 is a perspective view of an alternative embodiment of an upper member of a clamping device.

FIG. 10 illustrates another variation of an upper member 124 for use with the base member 22 in a clamping device 20 of the bone anchoring device 10. The upper member 124 includes a clamping surface 128, such as a convex surface, configured to mate with the clamping surface 26 of the base member 22 to clamp the flexible band 30 therebetween. The upper member 124 also includes a channel 150 extending through the upper member 124 from a first side 162 to a second side 164 configured to receive an elongate member, such as an elongate rod, of a stabilization construct therethrough. As shown in FIG. 10, the channel 150 may be a U-shaped channel defined between first and second arms 180, 182. The U-shaped channel 150 may open out upwardly at the upper terminal ends of the first and second arms 180, 182 to permit an elongate member, such as an elongate rod, to be inserted into the channel 150 in a top-loaded manner (e.g., in a direction generally transverse to the longitudinal axis of the channel 150). The first and second arms 180, 182 may include threads of a threaded bore 148 having a longitudinal axis extending transverse (e.g., perpendicular) to a longitudinal axis of the channel 150 such that the threaded bore 148 may intersect the channel 150. The threaded bore 148 may be configured to threadably engage the fastener 18 to bear against the elongate member extending through the channel 150 to secure the elongate member to the bone anchoring device 10 and lock the elongate member from axial and/or rotational movement relative to the upper member 124.

Figure 11:
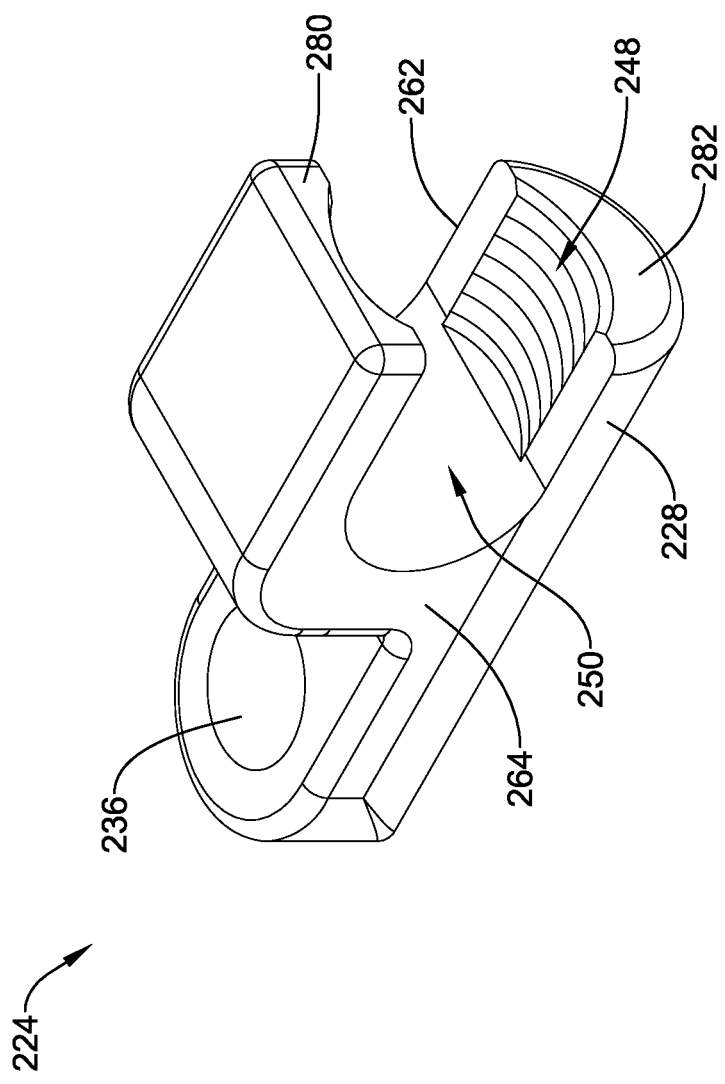
FIG. 11 is a perspective view of another alternative embodiment of an upper member of a clamping device.

FIG. 11 illustrates another variation of an upper member 224 for use with the base member 22 in a clamping device 20 of the bone anchoring device 10. The upper member 224 includes a clamping surface 228, such as a convex surface, configured to mate with the clamping surface 26 of the base member 22 to clamp the flexible band 30 therebetween. The upper member 224 also includes a channel 250 extending through the upper member 224 from a first side 262 to a second side 264 configured to receive an elongate member, such as an elongate rod, of a stabilization construct therethrough. As shown in FIG. 11, the channel 250 may be a U-shaped channel defined between first and second arms 280, 282. The U-shaped channel 250 may open out to the side of upper member 224 at the terminal ends of the first and second arms 280, 282 to permit an elongate member, such as an elongate rod, to be inserted into the channel 250 in a sideloaded manner (e.g., in a direction generally transverse to the longitudinal axis of the channel 250). The first and second arms 280, 282 may include threads of a threaded bore 248 having a longitudinal axis extending transverse (e.g., perpendicular) to a longitudinal axis of the channel 250 such that the threaded bore 248 may intersect the channel 250. The threaded bore 248 may be configured to threadably engage the fastener 18 to bear against the elongate member extending through the channel 250 to secure the elongate member to the bone anchoring device 10 and lock the elongate member from axial and/or rotational movement relative to the upper member 224.

Figure 12:
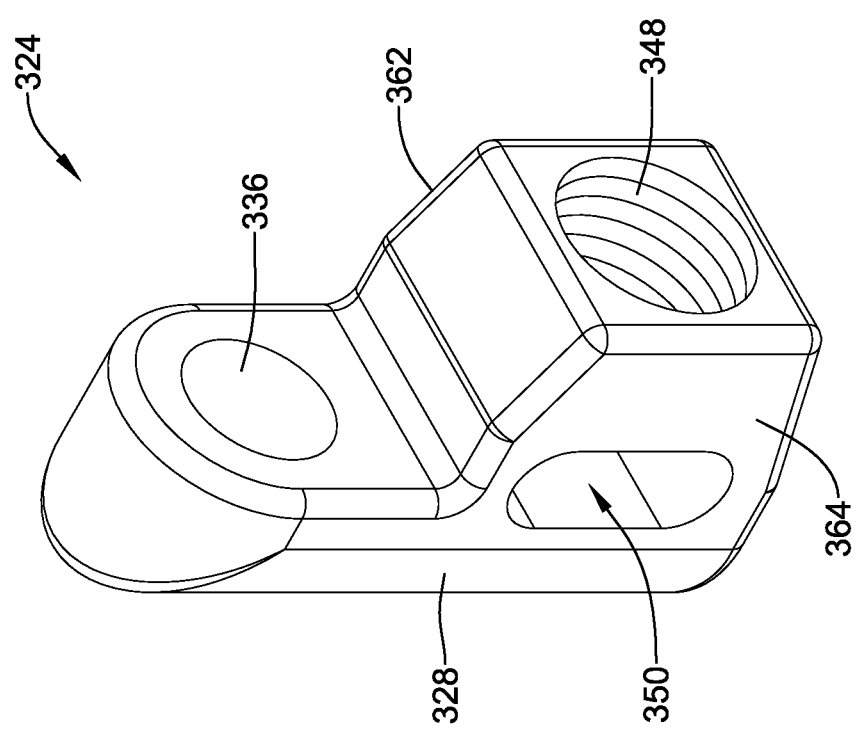
FIG. 12 is a perspective view of another alternative embodiment of an upper member of a clamping device.

FIG. 12 illustrates yet another variation of an upper member 324 for use with the base member 22 in a clamping device 20 of the bone anchoring device 10. The upper member 324 includes a clamping surface 328, such as a convex surface, configured to mate with the clamping surface 26 of the base member 22 to clamp the flexible band 30 therebetween. The upper member 324 also includes a channel 350, such as an elongated slot, extending through the upper member 324 from a first side 362 to a second side 364. The channel 350 may be configured to receive a stabilization component of a stabilization construct therethrough to secure the stabilization component to the upper member 324. In some instances, the channel 350 may be configured to receive the first end portion 32 and/or the second end portion 34 of the flexible band 30 therethrough when the flexible band 30 is used as a stabilization construct extending to one or more additional bone members, such as one or more adjacent vertebrae, for example. In other instances, the channel 350 may be configured to receive a wire therethrough when a wire is used to secure an implantable device to a spinal segment or otherwise used in a medical procedure. In some instances, the wire may be passed through the channel 350 and tied to the upper member 324. In some instances, the upper member 324 may also include a threaded bore 248 having a longitudinal axis extending transverse (e.g., perpendicular) to a longitudinal axis of the channel 350 which may intersect the channel 350. The threaded bore 348 may be configured to threadably engage the fastener 18 to bear against a stabilization component (such as the flexible band or a wire) extending through the channel 350 to secure the stabilization component to the bone anchoring device 10 and lock the stabilization component from axial and/or rotational movement relative to the upper member 324.

It can be seen from the figures that the channel 50, 150, 250, 350 for receiving a stabilization member of a vertebral stabilization construct may be offset from the passage 40 in the base member 22, and thus not in communication with the passage 40 when the upper member 24, 124, 224, 324 is assembled with the base member 22. For example, the passage 40 may be separated from the channel 50, 150, 250, 350 by a wall of the upper member 24, or otherwise not intersect or otherwise interconnect with the channel 50, 150, 250, 350. Thus, when the flexible band 30 is positioned through the passage 40 and clamped between the upper member 24 and the base member 22, the flexible band 30 may be spaced away from, and thus not directly contact the stabilization member, such as an elongate rod, the flexible band 30, or a wire, extending through and secured in the channel 50, 150, 250, 350. For instance, a wall of the upper member 24 may separate the flexible band 30 extending through the passage 40 from the portion of the stabilization member extending through the channel 50, 150, 250, 350.

Figure 13:
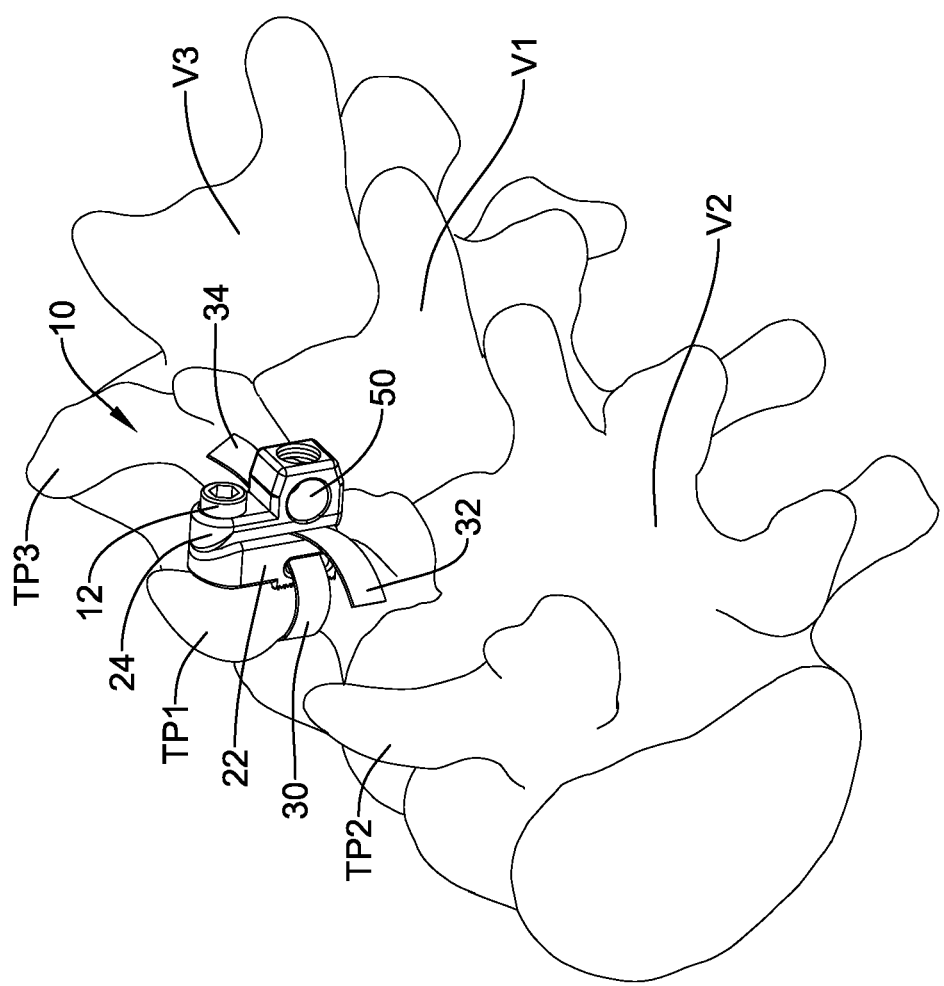
FIG. 13 illustrates an exemplary bone anchoring device secured to a bone member of a vertebra.

FIG. 13 illustrates the bone anchoring device 10 secured to a bone portion of a vertebra V1. The bone anchoring device 10 may be used in the cervical, thoracic, and/or lumbar spinal regions, as well as other regions of the body in which musculoskeletal correction and/or treatment is desired. Although the bone anchoring device 10 is illustrated as being secured to a transverse process TP of a vertebra V1, in other instances the bone anchoring device 10 may be secured to another bony anatomy in a similar fashion. For example, in some instances the bone anchoring device 10 may be secured to a spinous process, lamina, pedicle, rib, clavicle, long bone or other bone member, if desired.

As discussed above, the bone anchoring device 10 may be secured to a bone by passing the flexible band 30 around a portion of a bone and through the passage 40 of the clamping device 20. Once the flexible band 30 has been pulled tight to urge the clamping device 20 against the bone, the fastener 12 may be rotated to clamp the flexible band 30 between the clamping surface 26 of the base member 22 and the clamping surface 28 of the upper member 24. When tightly secured to the bone, the engagement surface 60 of the clamping device 20 may be pressed against the bone, while the flexible band 30 may extend around the opposite side of the bone and be cinched tightly to draw the engagement surface 60 into engagement with the bone and secure the bone anchoring device 10 from further movement. Accordingly, the bone anchoring device 10 may be rigidly secured to the bone to permit fixation of a stabilization construct to the bone without invasively altering or damaging the bone (e.g., without boring or screwing into the bone), or otherwise impairing the structural integrity of the bone.

Figure 14:
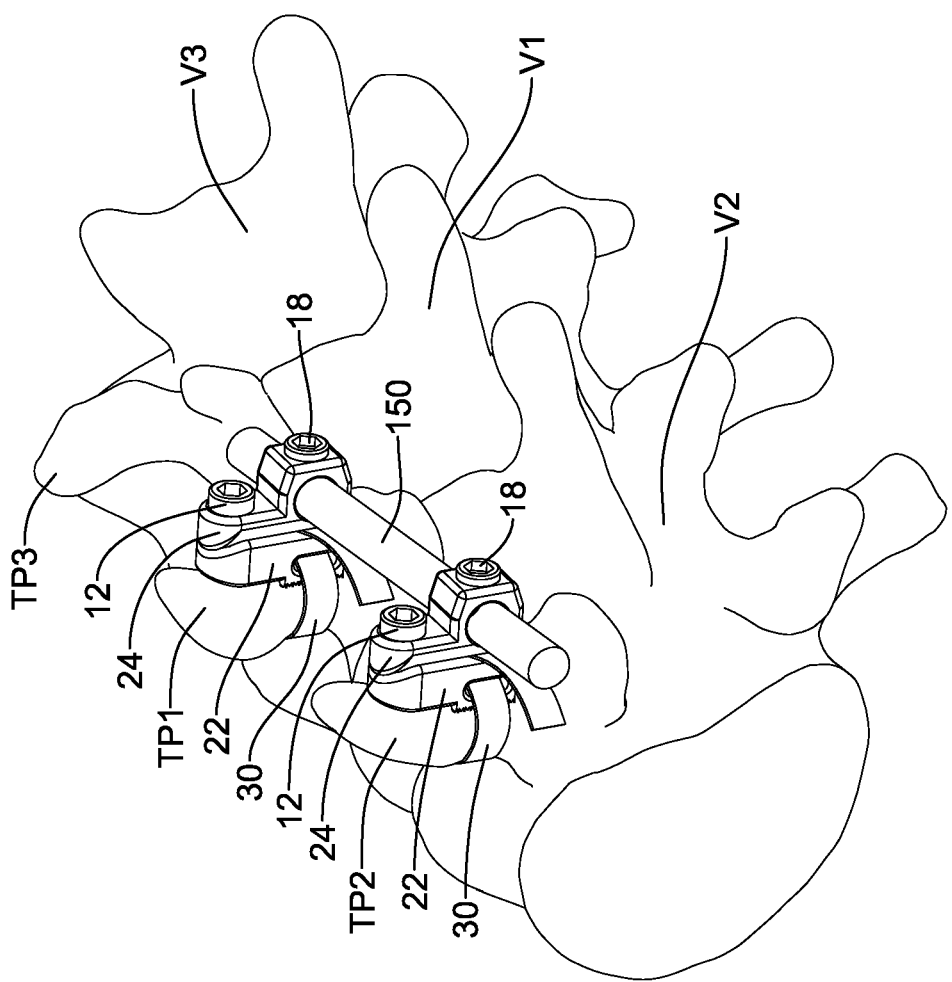
FIG. 14 illustrates an exemplary spinal stabilization construct secured to vertebrae with bone anchoring devices described herein.

FIG. 14 illustrates a spinal stabilization construct including an elongate member 150, such as an elongate rod, secured between a first vertebra V1 and a second vertebra V2 using a first bone anchoring member 10 secured to the transverse process TP1 of the first vertebra V1 and a second bone anchoring member 10 secured to the transverse process TP2 of the second vertebra V2. In some instances, in which the stabilization construct spans three or more vertebrae, an additional bone anchoring device 10 may be secured to the transverse process TP3 of the third vertebra V3, or an additional bone member, if desired. As shown in FIG. 14, the elongate member 150 may be positioned in the channels 50 of the upper members 24 of the clamping devices 20 and extend between the first bone anchoring device 10 secured to the first vertebra V1 and the second bone anchoring device 10 secured to the second vertebra V2. Once positioned in the channels 50, the threaded fasteners 18, such as set screws, may be tightened to lock the elongate member 150 from axial and/or rotational movement in the channels 50 of the clamping devices 20.

Figure 15:
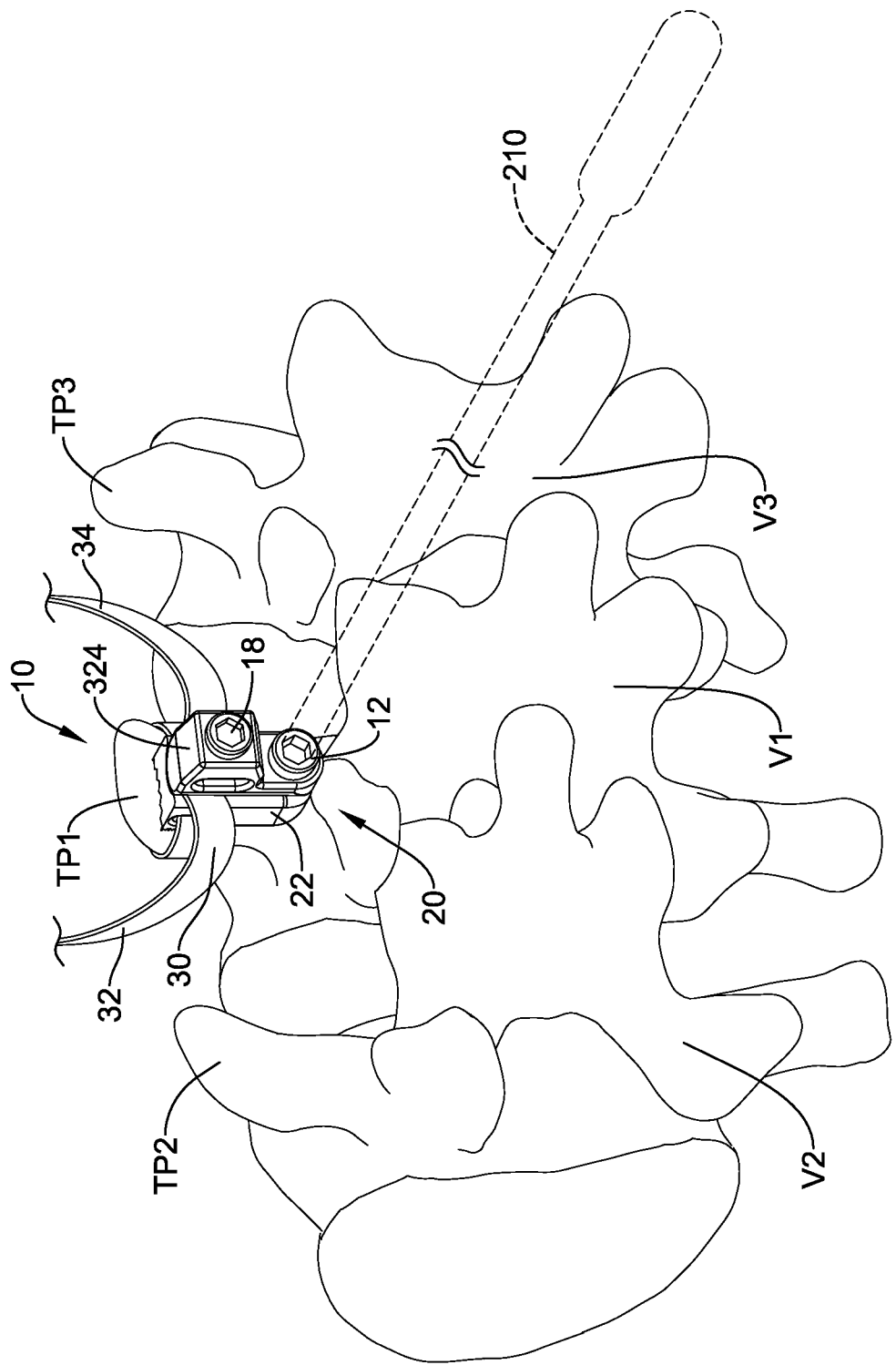
FIGS. 15-17 illustrate a method of securing a spinal stabilization construct to vertebrae including a bone anchoring device described herein.
Figure 16:
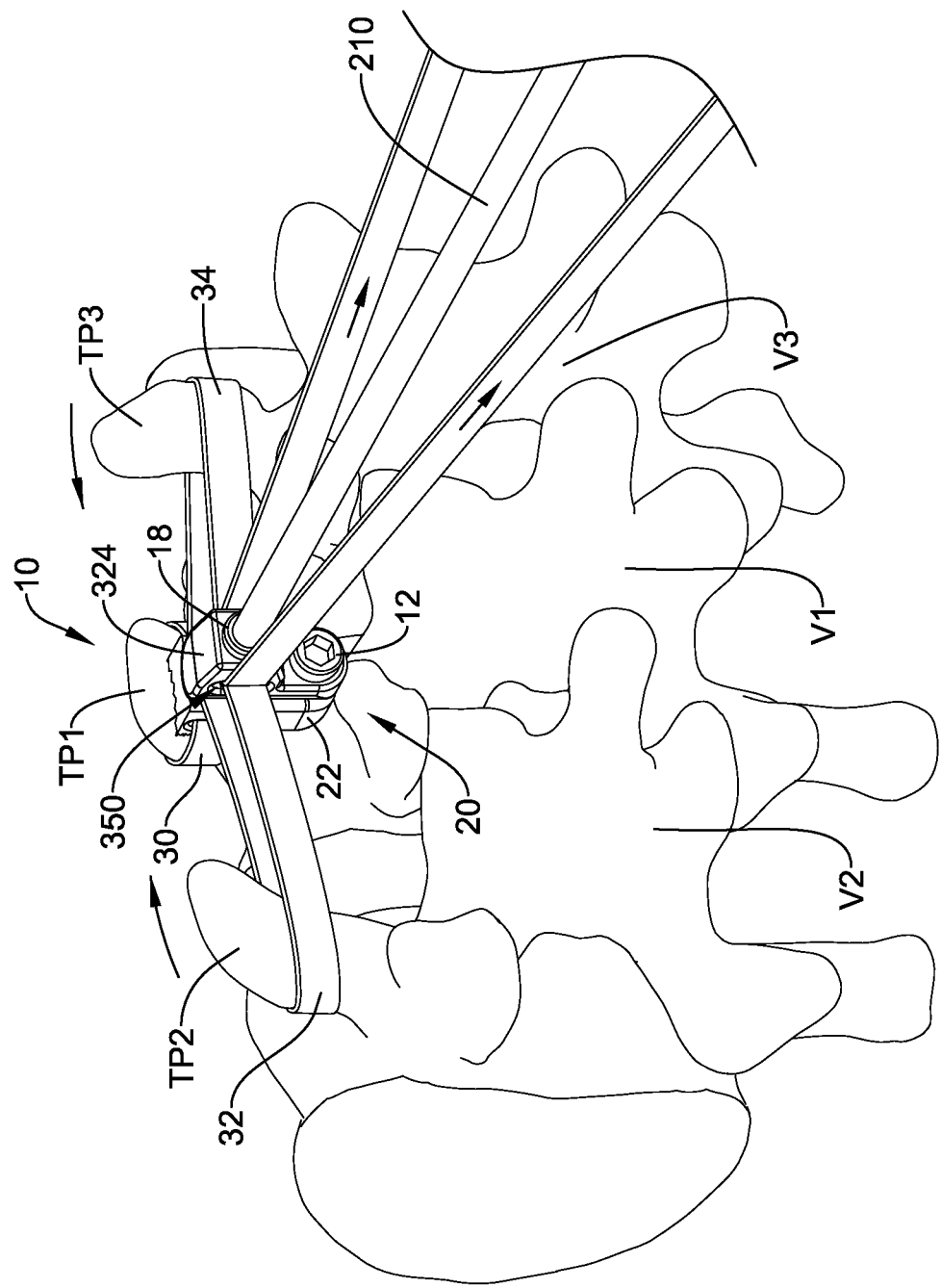
Figure 17:
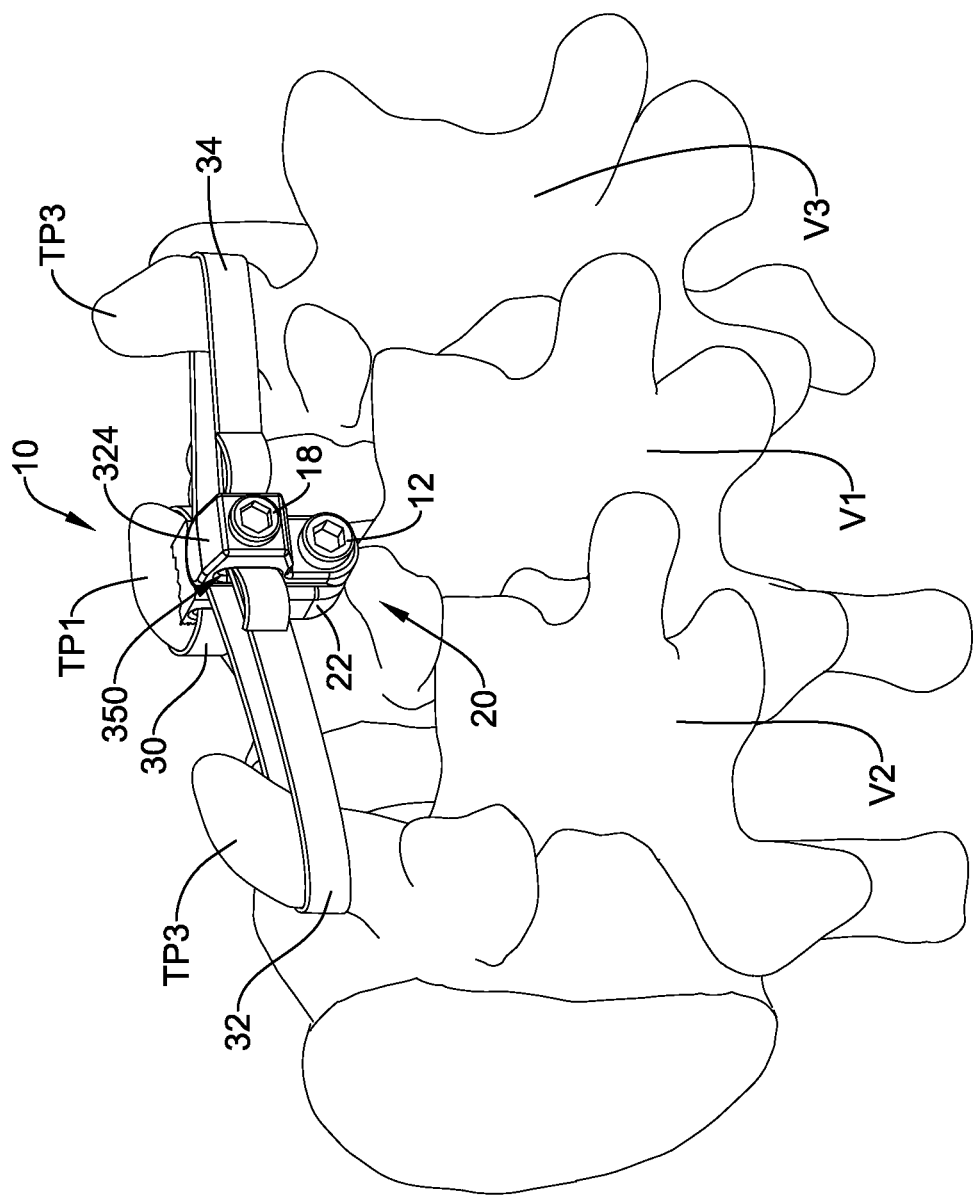

FIGS. 15-17 illustrate a method of correcting a curvature along a portion of a spinal column using the bone anchoring device 10. As shown in FIG. 15, a bone anchoring device 10 is first secured to a bone portion of a first vertebra V1, such as the transverse process TP1 of the first vertebra V1. To secure the bone anchoring device 10 to the transverse process TP1, the flexible band 30 is positioned around the transverse process TP1 of the first vertebra V1 with the clamping device 20 positioned against the transverse process TP1. Although the clamping device 20 is shown placed against a posterior aspect of the transverse process TP1, in other instances the clamping device 20 could be placed against an anterior aspect, a superior aspect, or an inferior aspect of the transverse process TP1, if desired. When used to correct the curvature of a portion of a spinal column, the clamping device 20 may be secured to a transverse process, or other bone structure, on the convex, outer curvature of the curved portion of the vertebral column to be corrected.

The flexible band 30, with the first end portion 32 of the flexible band 30 entering the passage 40 through the first opening 42 and exiting the passage 40 through the third opening 46 and the second end portion 34 of the flexible band 30 entering the passage 40 through the second opening 44 and exiting the passage 40 through the third opening 46 may then be tensioned using a tensioning device (not shown) to draw the intermediate portion of the flexible band 30 forming a loop around the transverse process TP1 between the first opening 42 and the second opening 44 taut to force the engagement surface 60 of the clamping device 20 against the transverse process TP1. While applying sufficient tension to the flexible band 30 to tightly secure the bone anchoring device 10 to the transverse process TP1, a driver 210 may be engaged with the fastener 12 and rotated to tighten the fastener 12 and thus clamp the upper member 24 to the base member 22. As the fastener 12 is tightened, the flexible band 30 is clamped between the clamping surface 26 of the base member 22 and the clamping surface 28 of the upper member 24 to prevent subsequent movement of the flexible band 30 through the passage 40 and thus lock the clamping device 20 from movement relative to the transverse process TP1.

Thereafter, as shown in FIG. 16, the first end portion 32 of the flexible band 30 may be extended around a bone portion of a second vertebra V2, such as a transverse process TP2 of the second vertebra V2 on the same lateral side of the spinal column as the transverse process TP1 of the first vertebra V1. The first end portion 32 is then advanced through the channel 350 of the upper member 324 from the first side of the upper member 324 facing the transverse process TP2 of the second vertebra V2 to the second side of the upper member 324 opposite the first side, forming a first secondary loop in the flexible band 30 extending around the transverse process TP2 from the passage 40 of the lower member 22 to the channel 350 of the upper member 324.

Additionally, the second end portion 34 of the flexible band 30 may be extended around a bone portion of a third vertebra V3, such as a transverse process TP3 of the third vertebra V3 on the same lateral side of the spinal column as the transverse process TP1 of the first vertebra V1. The second end portion 34 is then advanced through the channel 350 of the upper member 324 from the second side of the upper member 324 facing the transverse process TP3 of the third vertebra V3 to the first side of the upper member 324 opposite the second side, forming a second secondary loop in the flexible band 30 extending around the transverse process TP3 from the passage 40 of the lower member 22 to the channel 350 of the upper member 324. The first and second secondary loops of the flexible band 30 may extend along the convex, outer curvature of the spinal column.

As shown, the first vertebra V1, having the clamping device 20 secured thereto, may be positioned intermediate the second and third vertebrae V2, V3, such that the first secondary loop of the flexible band 30 extends in a first direction (e.g., superiorly or inferiorly) from the clamping device 20 while the second secondary loop of the flexible band 30 extends in a second, opposite direction (e.g., inferiorly or superiorly) from the clamping device 20. It is noted that in some instances it may be desirable to only provide one secondary loop of the flexible band 30 extending to another vertebra either superiorly or inferiorly of the clamping device 20.

The first end portion 32 of the flexible band 30 extending around the transverse process TP2 of the second vertebra V2 and the second end portion 34 of the flexible band 30 extending around the transverse process TP3 of the third vertebra V3 may then be simultaneously tensioned using a tensioning device (not shown) to draw the transverse process TP2 of the second vertebra V2 and/or the transverse process TP3 of the third vertebra V3 toward the clamping device 20 and thus the transverse process TP1 of the first vertebra V1 (shown by arrows in FIG. 16). While applying sufficient tension to the first and second end portions 32, 34 of the flexible band 30 to draw the transverse process TP2 of the second vertebra V2 and/or the transverse process TP3 of the third vertebra V3 toward the transverse process TP1 of the first vertebra V1, the driver 210 may be engaged with the fastener 18 and rotated to tighten the fastener 18 and thus clamp the first and second end portions 32, 34 of the flexible band 30 in the channel 350 of the upper member 324.

Thereafter, excess portions of the flexible band 30 may be trimmed, leaving the clamping device 20 secured to the first vertebra V1, and the first and second secondary loops of the flexible band 30 extending around bone portions of the second and third vertebrae, respectively, as shown in FIG. 17. Drawing the transverse process TP2 of the second vertebra V2 and/or the transverse process TP3 of the third vertebra V3 toward the transverse process TP1 of the first vertebra V1 tends to reduce the abnormal curvature of the spinal segment to be corrected, and thus tends to straighten an abnormal curvature of the spinal column.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A bone anchoring device comprising:
   a clamping device including:
      a passage extending therethrough;
      a channel extending therethrough, for receiving a stabilization member of a vertebral stabilization construct;
      a bone engagement surface configured to engage a surface of a bone member when secured thereto, the bone engagement surface including engagement features to enhance frictional engagement between the bone engagement surface and the surface of the bone member; and
   a flexible band extendable through the passage of the clamping device and configured to be passed around the bone member to secure the clamping device to the bone member with the bone engagement surface pressed against the surface of the bone member.

2. The bone anchoring device of claim 1, wherein the bone engaging surface is configured to press into a bone member when the flexible band is tightened around the bone member.

3. The bone anchoring device of claim 1, wherein the engagement features include surface roughening features configured for gripping the bone member.

4. The bone anchoring device of claim 3, wherein the engagement features include one or more teeth configured to engage the bone member.

5. The bone anchoring device of claim 3, wherein the engagement features include a layer of a porous metal defining a plurality of pores.

6. The bone anchoring device of claim 3, wherein the engagement features include one or more grooves.

7. The bone anchoring device of claim 1, wherein the clamping device includes a base member and an upper member configured to be secured together with a fastener.

8. The bone anchoring device of claim 7, wherein the base member includes the bone engagement surface.

9. The bone anchoring device of claim 7, wherein the base member includes the passage for receiving the flexible band therethrough.

10. The bone anchoring device of claim 7, wherein the upper member includes the channel.

11. The bone anchoring device of claim 7, wherein the flexible band is positionable between a clamping surface of the base member and a clamping surface of the upper member.

12. The bone anchoring device of claim 11, wherein the clamping device includes a first fastener for clamping the flexible band between the clamping surface of the base member and the clamping surface of the upper member.

13. The bone anchoring device of claim 12, wherein the clamping device includes a second fastener for clamping a stabilization member in the channel.

14. The bone anchoring device of claim 1, wherein the clamping device includes a first fastener for clamping the flexible band in the passage.

15. The bone anchoring device of claim 14, wherein the flexible band is clamped in the passage independent of clamping a stabilization member in the channel.

16. The bone anchoring device of claim 14, wherein the clamping device includes a second fastener for clamping a stabilization member in the channel.

17. The bone anchoring device of claim 1, wherein the passage includes a first opening on a first side of the clamping device and a second opening on a second side of the clamping device, opposite the first side, a first end portion of the flexible band extendable through the first opening and a second end portion of the flexible band extendable through the second opening, with a loop portion of the flexible band extendable around the bone member.

18. The bone anchoring device of claim 1, wherein the bone engagement surface is a concave surface.

19. The bone anchoring device of claim 1, wherein the channel is offset from the passage.

\* \* \* \* \*